United States Patent
Amasino et al.

(10) Patent No.: US 9,451,754 B2
(45) Date of Patent: *Sep. 27, 2016

(54) **SELF-COMPATIBLE, RAPID-CYCLING *BRASSICA RAPA* PLANTS LACKING INBREEDING DEPRESSION**

(71) Applicant: Wisconsin Alumni Research Foundation, Madison, WI (US)

(72) Inventors: Richard M. Amasino, Madison, WI (US); Scott Woody, Windsor, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 307 days.

This patent is subject to a terminal disclaimer.

(21) Appl. No.: 14/026,955

(22) Filed: Sep. 13, 2013

(65) Prior Publication Data

US 2014/0090097 A1  Mar. 27, 2014

Related U.S. Application Data

(63) Continuation of application No. 12/781,705, filed on May 17, 2010, now Pat. No. 8,629,329.

(60) Provisional application No. 61/179,711, filed on May 19, 2009.

(51) Int. Cl.
*A01H 5/10* (2006.01)
*A01G 1/00* (2006.01)

(52) U.S. Cl.
CPC *A01H 5/10* (2013.01); *A01G 1/00* (2013.01); *A01G 1/001* (2013.01)

(58) Field of Classification Search
None
See application file for complete search history.

(56) References Cited

U.S. PATENT DOCUMENTS

| | | | |
|---|---|---|---|
| 4,950,166 A | 8/1990 | Williams | |
| 5,107,064 A | 4/1992 | Williams et al. | |
| 5,508,184 A | 4/1996 | Negrutiu et al. | |
| 6,297,056 B1 | 10/2001 | Tulsieram et al. | |
| 2010/0319080 A1 | 12/2010 | Amasino et al. | |

OTHER PUBLICATIONS

Williams et al, Science 232: 1385-1389, 1986.*
Fujimoto et al, FEBS Lett 580 (2): 425-430, 2006.*
Amasino et al., "Development of rapid-cycling brassica rapa as a model for teaching genetics," Joint Ann. Meeting of the Amer. Fern Society/ Amer. Society of Plant Biologists/Amer. Society of Plant Taxonomist/Botanical Society of America, Chicago, Jul. 7, 2007.
Cruz et al., "Characterization of flowering time and SSR marker analysis of spring and winter type brassica napus L. germplasm," *Euphytica*, 153:43-57, 2007.
Devitt, "Plants speed science education," www.news.wisc.edu/7728, dated Aug. 19, 2002.
Devlin et al., "The brassica rapa elongated internode (EIN) gene encodes phytochrome B," Plant Mol. Biol., 34:537-547, 1997.
Friend et al., "Brassica campestris L.: floral induction by one long day," *Sci.*, 153(3740):1115-1116, 1966.
Friend, "Photoperiodic responses of brassica campestris cv. Ceres," *Physiologia Plantarum*, 21(5):990-1002, 1968.
Fujimoto et al., FEBS Lett 580(2); 425-430, 2006.
Muangprom etal., "Transfer of a dwarf gene from brassica rapa to oilseed *B. napus*, effects on agronomic traits, and development of a 'perfect' marker for selection," *Mol. Breed.*, 17:101-110. 2006.
Waller et al., "Effects of stress and phenotypic variation on inbreeding depression in brassica rapa," *Evolution*, 62:917-931, 2008.
Williams et al.,"Rapid-cycling populations of brassica," *Sci.*, 232:1385-1389, 1986.
Zanewich et al., "Dwarf mutants of brassica: responses to applied gibberellins and gibberellin," *J. of Plant Growth Regulation*, 10(1-4):121-127, 1991.

* cited by examiner

*Primary Examiner* — Elizabeth McElwain
(74) *Attorney, Agent, or Firm* — Dentons US LLP

(57) ABSTRACT

The invention provides *Brassica rapa* plants and seeds thereof that are self-compatible, rapid-cycling and lack inbreeding depression. For instance, the invention provides plants and seeds of the *Brassica rapa* line designated B3. The invention thus relates to plants, seeds and tissue cultures of *Brassica rapa* plants that are self-compatible, rapid-cycling and lack inbreeding depression, such as *Brassica rapa* line B3, and methods to produce and propagate said plants by crossing such a *Brassica rapa* plant with itself, or another *Brassica rapa* plant. The invention further relates to seeds and plants produced by such crossing. Educational materials, such as a kit comprising said *Brassica rapa* plants are also provided by the invention.

22 Claims, 2 Drawing Sheets

SELF-COMPATIBLE, RAPID-CYCLING BRASSICA RAPA PLANTS LACKING INBREEDING DEPRESSION

CROSS-REFERENCE TO RELATED APPLICATIONS

This application is a continuation of U.S. application Ser. No. 12/781,705, filed May 17, 2010, which application claims the benefit of priority of U.S. Provisional Application Ser. No. 61/179,711, filed on May 19, 2009, each of the entire disclosures of which are incorporated herein by reference in their entireties.

This invention was made with government support under 0446440 awarded by the National Science Foundation. The government has certain rights in the invention.

BACKGROUND OF THE INVENTION

I. Field of the Invention

The present invention relates to rapid-cycling plants that are self-compatible and lack inbreeding depression. Also disclosed are methods of producing and using such plants.

II. Description of Related Art

There exist several model systems for education and research in genetics such as Arabidopsis, zebrafish, C. elegans and Drosophila, but these model systems pose difficulties for educators' use. Among the reasons these model systems are difficult to use are the space and time required for growing and breeding, which classroom or small laboratory environments lack, as well as hindering physical characteristics and the requirement for additional equipment and time for phenotyping and mating. For instance, genetic experiments utilizing plants as model organisms often require multiple crosses to produce a useful number generations displaying identifiable pheonotypes. Production of teaching lines and the use of these lines in the classroom therefore requires months or even years to perform cross-breedings of individual plants with desired traits, as many plants have lengthy life cycles. Similarly, the space required to perform the necessary number of breedings to produce or use such lines is prohibitive for classroom or small laboratory environments. The available model systems are therefore not ideal for use in educational environments.

For instance, Arabidopsis plants possess small seeds and flowers and exhibit extensive branching that easily becomes entangled making it difficult to track individual plants. These plants are thus not a useful system for all ages of students. Drosophila are difficult to use as well due to the need to anesthetize the organisms when determining phenotype, the timing of matings, and the need for magnification to view phenotypes.

SUMMARY OF THE INVENTION

In one aspect, the invention provides a Brassica rapa plant that is self-compatible, rapid-cycling and lacks inbreeding depression. In one embodiment, the plant is a plant of line B3 or a progeny thereof. In another embodiment, the plant is inbred.

In certain aspects, the invention provides a plant part of a Brassica rapa plant that is self-compatible, rapid-cycling and lacks inbreeding depression. In one embodiment, the plant part is selected from the group consisting of a protoplast, ovule, cell, pollen grain, embryo, cotyledon, hypocotyl, meristem, root, pistil, anther, flower, stem, pod or petiole. In another aspect, the invention provides a tissue culture of regenerable cells of a Brassica rapa plant that is self-compatible, rapid-cycling and lacks inbreeding depression. In a particular embodiment, the tissue comprises cells or protoplasts from a plant part selected from the group consisting of embryos, meristems, cotyledons, pollen, leaves, anthers, roots, root tips, shoots, pistil, flower, seed and stem.

In yet another aspect, the invention provides a method of propagating a Brassica rapa plant that is self-compatible, rapid-cycling and lacks inbreeding depression, comprising crossing the plant with itself or a second plant to which the Brassica rapa plant is capable of being crossed. In one embodiment, the second plant is self-compatible and rapid-cycling. The second plant may also lack inbreeding depression or be defined as lacking alleles that confer inbreeding depression. In a further aspect, the present invention provides a method of vegetatively propagating a Brassica rapa plant of the invention comprising: (a) collecting tissue capable of being propagated from a Brassica rapa plant that is self-compatible, rapid-cycling and lacks inbreeding depression; (b) cultivating the tissue to obtain proliferated shoots; and (c) rooting the proliferated shoots to obtain rooted plantlets. In particular embodiments, the method further comprises growing plants from the rooted plantlets.

In still yet another aspect, the invention provides a method of producing progeny comprising crossing a plant of the invention with itself of a second plant. The second plant may be a Brassica rapa plant that is self-compatible, rapid-cycling and lacks inbreeding depression. In particular embodiments the method may comprise selecting at least a first progeny plant that comprises a desired trait. In a further aspect, the invention provides a plant produced by this method. In a certain embodiment, the method further comprises: (c) backcrossing the selected first progeny plant from step (b) with a plant that is self-compatible, rapid-cycling and lacks inbreeding depression; and (d) selecting at least a first backcross progeny plant from step (c) that comprises the desired trait.

In a further embodiment, the desired trait is selected from the group consisting of a pigmentation-defective mutant trait and developmental mutant trait. In another embodiment, the desired trait is selected from the group consisting of embryo lethal, albino, leaf shape, leaf number, leaf color, variegated leaf, flower shape, flower number, flower color, seed color, seed shape, tissue- or organ-specific pigmentation, a photosynthesis trait, internode shape, hypocotyl shape, cotyledon shape, stem shape, pod shape, dwarf and over-sized. In yet another embodiment, the desired trait is due to a mutation in a gene encoding a protein involved in a biochemical or developmental pathway.

In still yet another aspect, the invention provides an educational kit comprising a Brassica rapa plant, or propagating material of such a plant, that is self-compatible, rapid-cycling and lacks inbreeding depression. In a further aspect, the invention provides a Brassica rapa plant of line B3, further comprising a single locus conversion, wherein the plant otherwise comprises essentially all of the physiological and morphological characteristics of Brassica rapa line B3.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments.

DETAILED DESCRIPTION OF THE INVENTION

The present invention provides novel rapid-cycling, self-compatible, self-fertile *Brassica rapa* (*B. rapa*) plants lacking inbreeding depression. *Brassica rapa* plants provided by the present invention, including plants of the line B3, have a rapid reproductive cycle and are capable of self-pollination. Thus, the plants described herein can be reproduced by planting and growing seeds of the plants under self-pollinating or sib-pollinating conditions, as are known to those of skill in the agricultural arts. In one embodiment, the plants of the present invention have easily detectable phenotypic traits that can be quantified without difficulty. Because the plants are rapid-cycling, multiple generations can be produced and studied in a short time. Additionally, no special equipment such as microscopes, aquariums or other special breeding equipment or large greenhouses is needed to grow, cross and study the plants.

The presently described plants were selected for size, rapid-cycling, and self-compatibility. In one embodiment, the plants of the invention are inbred resulting in homozygosity at essentially all loci in the plant's genome. The developed lines therefore demonstrate traits desirable in a plant, such as, maintained fitness when self-pollinated, little to no inbreeding depression, a desirable height and a healthy appearance. *Brassica rapa* line B3 is one such example that maintains viability in a commercial, laboratory or classroom setting.

Figure 1:
FIG. 1: Photographic comparison of a mature *Arabidopsis* plant (right) and a rapid-cycling *Brassica rapa* of the present invention (left) demonstrating the extensive branching and intermingling of *Arabidopsis* flowering stalks compared to the single main stalk of *Brassica rapa*.

The *Brassica rapa* plants of the present invention provide an improvement over the currently existing model systems for education and research in genetics, such as *Arabidopsis*, zebrafish, *C. elegans* and *Drosophila*, as these model systems are difficult for educators to use due to long life cycles or hindering physical characteristics. For instance, the small seeds and flowers of *Arabidopsis* plants render planting and cross-pollination difficult. Additionally, *Arabidopsis* is structurally complex with extensive branching and elongated stems that intertwine and thus hinder keeping track of individual plants grown at high densities, it is therefore not useful in settings with limited space, such as classrooms or small laboratories and thus is not conducive to teaching (FIG. 1). *Drosophila* and *C. elegans* are also difficult to use in a classroom setting, as they must be anesthetized to determine phenotype and timing of matings. *Drosophila* additionally require magnification to view phenotypes, requiring special equipment and excess time.

Alternative classroom models, including self-incompatible models, such as Wisconsin Fast Plants, lack the capacity to self-fertilize, requiring additional space and time to perform the necessary sib-pair matings. The rapid-cycling *Brassica rapa* plants of the current invention, however, are self-compatible and thus require less breeding effort and greenhouse space to do large-scale mutagenesis than a self-incompatible model organism would. For instance, in order to create lines with differing phenotypes through large scale mutagenesis, self-incompatible plants require extensive sib-pair matings and thus a prohibitive amount of effort and greenhouse space. Although methods exist to permit self-fertilization of such plants, these methods are difficult and thus impractical for implementation by teachers and students. Furthermore, even if such approaches were used to bypass self-incompatibility mechanisms, the considerable level of heterozygousity maintained in the genome of such self-incompatible plants has demonstrated the potential for inbreeding depression. Plants of the current invention are therefore better suited to teach concepts in developmental biology or biochemical genetics than the currently available classroom models.

In one embodiment of the present invention, the plants of the present invention are inbred providing an advantage as a genetic model over the currently available classroom models. For instance, inbred lines will ordinarily be phenotypically uniform and thus any phenotypic variation in mutant plants is readily apparent. Additionally, a high level of inbreeding will decrease the number of loci in which the plants of the present invention are heterozygous, which is beneficial for molecular based approaches to study the concepts of linkage and inheritance. However, plants that maintain a considerable level of heterozygosity, for instance, self-incompatible model plants, are not ideal for such molecular approaches due to the presence of multiple alleles at many loci in the genome.

I. BREEDING *Brassica rapa* PLANTS

One aspect of the current invention concerns methods for crossing a *Brassica rapa* plant of the invention with itself or a second plant and the plants and seeds produced by such methods. These methods can be used for propagation of the *Brassica rapa* plants or can be used to produce new or mutant *Brassica rapa* plants and seeds therefrom. Hybrid seeds can be produced by crossing a *Brassica rapa* plant such as a plant of line B3 with a second, distinct *Brassica rapa* plant. A mutant *Brassica rapa* plant can be derived from a starting *Brassica rapa* plant to obtain a plant that displays a selected mutant phenotype or trait. A mutant plant can be used as a recurrent parent at any given stage in a backcrossing protocol during the production of a self-compatible, rapid-cycling, *Brassica rapa* plant.

In one aspect of the invention, a plant provided herein will be used to create mutant lines, which in one embodiment, may be used as classroom teaching aids to teach principals of molecular biology and genetics. The development of mutant lines using one or more starting lines is well known in the art. In one embodiment, a M1 generation is created through mutagenesis of a *Brassica rapa* plant according to methods well known in the art. For instance, in one embodiment, *Brassica rapa* plant cells are subjected in at least one generation to mutagenesis, and a *Brassica rapa* plant is grown from mutagenized seeds or otherwise regenerated from the cells to produce a mutant *Brassica rapa* plant. Following mutagenesis, substantial genetic homogeneity may be achieved via self-pollination for a sufficient number of generations (e.g., 2 to 8 generations) to fix the desired mutant trait. In certain embodiments, additional generations of backcrossing are then performed to purge the genome of unrelated lesions induced by mutagenesis.

One embodiment of the invention involves mutagenesis that may be accomplished by subjecting the plant cells to a technique selected from the group consisting of contact with a chemical mutagen, irradiation, and a combination of the foregoing, for a sufficient duration to accomplish the desired genetic modification but insufficient to completely destroy the viability of the cells and their ability to be regenerated into a plant. The desired mutagenesis may be accomplished by use of chemical means, such as by contact with ethylmethylsulfonate, ethylnitrosourea, etc., or by the use of physical means, such as x-rays, etc. Mutagenesis also may be carried out by gamma radiation, such as that supplied by a Cesium 137 source. In some embodiments, gamma radiation may be supplied to the plant cells in a dosage of approximately 60 to 200 Krad., or in a dosage of approximately 60 to 90 Krad. It should be understood that even when operating at radiation dosages within the ranges specified, some plant cells may completely lose their viability and must be discarded.

It will be appreciated that the mutagenesis treatment potentially will result in a wide variety of genetic changes within the *Brassica rapa* plants which are produced. Many of these changes may be deleterious to the viability of the resulting plant over an extended period of time. Some changes will produce viable plants which possess deficient agronomic characteristics. Such off-types may be simply discarded or may be retained if phenotypes are useful for teaching purposes. Alternatively, plants which have undergone the desired mutation production coupled with undesirable agronomic traits can be retained and used as breeding or source material from which plants having the targeted traits coupled with satisfactory agronomic characteristics ultimately are derived by plant breeding. Following mutagenesis, *Brassica rapa* plants are regenerated from the treated cells using known techniques to create a M1 generation.

In accordance with the invention, novel mutant lines may then be created by crossing a plant from the M1 generation to itself or to a second plant, including a *Brassica rapa* plant of line B3. Once initial crosses have been made, inbreeding and selection may take place to produce the new lines. For development of a uniform line, often five or more generations of selfing and selection are involved.

Any time a *Brassica rapa* plant is crossed with another, distinct, *Brassica rapa* plant first generation (F1) *Brassica rapa* progeny are produced. The hybrid progeny are produced regardless of characteristics of the two lines produced. As such, an F1 hybrid *Brassica rapa* may be produced by crossing a *Brassica rapa* of line B3 with any *Brassica rapa* plant of a different genotype. The second *Brassica rapa* plant may be genetically homogeneous (e.g., inbred) or may itself be a hybrid. Therefore, any F1 hybrid *Brassica rapa* plant produced by crossing a *Brassica rapa* plant of the invention with a second *Brassica rapa* plant is a part of the present invention.

Choice of breeding or selection methods depends on the mode of plant reproduction, the heritability of the trait(s) being selected for, and the type of plant line used (e.g., M1 mutant, F1 hybrid, pureline, etc.). For highly heritable traits, a choice of superior individual plants evaluated at a single location will be effective, whereas for traits with low heritability, selection should be based on mean values obtained from replicated evaluations of families of related plants. Breeding methods commonly used are known in the art. For instance, popular selection methods commonly include backcrossing, pedigree selection, modified pedigree selection, mass selection and recurrent selection.

Backcrossing can be used to introduce a specific desirable trait from one inbred or non-inbred source to an inbred that lacks the desirable trait. This can be accomplished, for example, by first crossing a recurrent parent to a donor inbred or non-recurrent parent, which carries the trait in question. The resulting plant is expected to have the attributes of the recurrent parent and the desirable trait transferred from the donor parent. The progeny of the initial cross are then repeatedly crossed to the recurrent parent (backcrossed) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred. In one aspect of the invention the trait to be introduced is a mutant trait, such as embryo lethal, albino, leaf shape, leaf number, leaf color (including variegated), flower shape, flower number, flower color, seed color, seed shape, tissue- or organ-specific pigmentation, a photosynthesis trait, internode shape, hypocotyl shape, cotyledon shape, stem shape, pod shape, and dwarf and over-sized plants.

Pedigree breeding and recurrent selection breeding methods are used to develop varieties from breeding populations. Breeding programs combine desirable traits from two or more varieties or various broad-based sources into breeding pools from which varieties are developed by selfing and selection of desired phenotypes. The new varieties are evaluated to determine which have a desired phenotype.

Pedigree breeding is commonly used for the improvement of self-pollinating plants. Two parents which possess favorable, complementary traits are crossed to produce an F1. An F2 population is produced by selfing one or several F1 plants. Selection of the best individuals may begin in the F2 population (or later depending upon the breeder's objectives); then, beginning in the F3 generation, the best individuals in the best families can be selected. Replicated testing of families can begin in the F3 or F4 generation to improve the effectiveness of selection for traits with low heritability. At an advanced stage of inbreeding (i.e., F6 and F7), the best lines or mixtures of phenotypically similar lines are tested for potential release as new varieties.

Mass and recurrent selections can be used to improve populations of either self- or cross-pollinating plants. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, collecting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

*Brassica rapa* plants can be crossed by either natural or mechanical techniques. Natural cross-pollination typically is aided by pollinating organisms. Hand pollination can be carried out by removing the stamens and pistil with a forceps from a flower of the male parent and gently brushing the anthers against the stigma of the female flower or any other method that adequately transfers pollen from the male plant to the female flower. Access to the stamens can be achieved by removing the front sepal and keel petals, or piercing the keel with closed forceps and allowing them to open to push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

II. FURTHER EMBODIMENTS OF THE INVENTION

In certain embodiments of the invention, plants are provided that are modified to include at least a first desired heritable trait. Such plants may, in one embodiment, be developed by a plant breeding technique called backcrossing, wherein essentially all of the morphological and physiological characteristics of one line are recovered in addition to a desired trait transferred into the plant via the backcrossing technique. By "essentially all of the morphological and physiological characteristics" it is meant that the traits of the recurrent parent are recovered other than an occasional variant trait.

Backcrossing methods can be used with the present invention to improve or introduce a characteristic into the present lines. The parental *Brassica rapa* plant which contributes the desired characteristic is termed the non-recurrent or donor parent. This terminology refers to the fact that the non-recurrent parent is used one time in the backcross protocol and therefore does not recur. The parental *Brassica rapa* plant to which the desired trait from the non-recurrent parent are transferred is known as the recurrent parent as it is used for several rounds in the backcrossing protocol.

In a typical backcross protocol, the original line of interest (recurrent parent) is crossed to a second line (non-recurrent parent) that carries the trait of interest to be transferred. The resulting progeny from this cross are then crossed again to the recurrent parent and the process is repeated until a *Brassica rapa* plant is obtained wherein essentially all of the desired morphological and physiological characteristics of the recurrent parent are recovered in the converted plant, in addition to the transferred trait from the non-recurrent parent.

The selection of a suitable recurrent parent is an important step for a successful backcrossing procedure. The goal of a backcross protocol is to alter or substitute a single trait or characteristic in the original line. To accomplish this, the desired trait of the non-recurrent line is introgressed into the recurrent parent, while retaining essentially all of the rest of the desired physiological and morphological constitution of the original line. The choice of the particular non-recurrent parent will depend on the purpose of the backcross; one of the major purposes is to add some commercially desirable trait to the plant. The exact backcrossing protocol will depend on the characteristic or trait being altered.

*Brassica rapa* lines can also be developed from more than two parents. The technique, known as modified backcrossing, uses different recurrent parents during the backcrossing. Modified backcrossing may be used to replace the original recurrent parent with a line having certain more desirable characteristics or multiple parents may be used to obtain different desirable characteristics from each.

Selection of *Brassica rapa* plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of *Brassica rapa* are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

III. TISSUE CULTURES AND IN VITRO REGENERATION OF *Brassica rapa* PLANTS

A further aspect of the invention relates to tissue cultures of the *Brassica rapa* line B3. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In one embodiment, the tissue culture comprises embryos, protoplasts, cotyledons, meristematic cells, pollen, leaves, anthers, roots, root tips, shoots, pistil, flower, seed or stem.

Exemplary procedures for preparing tissue cultures of regenerable *Brassica rapa* cells and regenerating *Brassica rapa* plants therefrom, are disclosed in U.S. Pat. No. 5,508,184 and U.S. Pat. No. 6,297,056, the disclosures of which are specifically incorporated herein by reference in their entirety.

An important ability of a tissue culture is the capability to regenerate fertile plants. This allows, for example, for vegetative propagation of the *Brassica rapa* plants of the invention by collecting tissue capable of being propagated, cultivating said tissue to obtain proliferated shoots, rooting said proliferated shoots to obtain rooted plantlets, and growing plants from said rooted plantlets.

IV. EDUCATIONAL KITS

Also provided by the present invention is an educational kit constructed to utilize the rapid-cycling plants from the presently described *Brassica rapa* lines, for instance, line B3 and mutants derived therefrom. In one embodiment, the educational kit comprises a quantity of rapid-cycling *Brassica rapa* plants or seeds of the invention, which, in one aspect, may have a phenotype of educational interest. The kit may additionally include materials necessary to grow and breed the plants. For instance, a compact plant growth environment including a physical container for receiving plants therein and a continuous watering system capable of providing liquid to plants in the container may be included in the educational kit. In one aspect, the kit may also include additional supplies for the growth of the rapid-cycling *Brassica rapa* plants such as clear plastic support separators, pre-cut squares of cheese cloth for germination, watering pipette for initial watering and chemical treatments, a trellis onto which the plants may climb and a completed soil mixture.

In another embodiment, within the kit, there would additionally be various materials appropriate for any given experiment. For example, for an experiment related to a specific trait or the demonstration of Mendelian inheritance, the specific seed stocks would need to be selected for their individual observable phenotypes as related to a particular experiment. Plant nutrients or hormonal plant growth regulators could be supplied to demonstrate their effect on plant growth. Antibiotics or herbicides could be supplied in small doses to demonstrate their adverse effect on plant growth as could parasites, pests or pathogens. Competitiveness could be determined by growing stocks together in the same pot or by including weed seeds selected to provide competition to the *Brassica rapa* populations with the kit. Other biological symbionts could be provided to demonstrate their effects, either adverse or positive, on the growing plant populations In yet another embodiment, for any given experiment to be formed for educational purposes with the rapid-cycling populations, one or more of a number of experimental supplies may be necessary. Among these supplies could be rubbing alcohol, which would be useful for sterilizations, tweezers, which are useful for thinning plants during the growth cycle, and a pollination tool, such as a bee stick. A bee stick is a toothpick with the thorax of a honey bee glued on one end so as to make use of the pollen gathering character of the hairy thorax of a bee. The fabrication and use of bee sticks is described in detail in Williams, "Bee-Sticks, an Aid in Pollinating Cruciferae," *Horticulture*, 15(6), p. 802-803, December 1980. The bee sticks could be supplied preassembled or could be supplied in parts to be assembled by the students from bee cadavers, toothpicks and glue.

In another embodiment, the educational kit of the present invention use would also include appropriate documentation. The documentation would include detailed teacher and student instructions on the husbandry of the *Brassica rapa* plants as well as instructions on how to perform the demonstration or experiment of the particular kit. In addition, the documentation would preferably include general botanical information on the history and uses of *Brassica rapa* and other relevant background information to enrich student and teacher learning.

V. DEFINITIONS

In the description a number of terms are used. In order to provide a clear and consistent understanding of the specification and claims, the following definitions are provided:

Backcrossing: A process in which a breeder repeatedly crosses hybrid progeny, for example a first generation hybrid (F1), back to one of the parents of the hybrid progeny. Backcrossing can be used to introduce one or more desired trait from one genetic background into another.

Crossing: The mating of two parent plants by pollination of a female flower.

Cross-pollination: Fertilization by the union of two gametes from different plants.

Inbreeding Depression: The reduced fitness or vigor in a plant, resulting from inbreeding. In one embodiment inbreeding depression may result in reduced size, health and/or fertility. In another embodiment, a plant lacking inbreeding depression substantially maintains phenotypic characteristics of an outcrossed background when bred to generate an inbred background.

Linkage: A phenomenon wherein alleles on the same chromosome tend to segregate together more often than expected by chance if their transmission was independent.

Phenotype: The detectable characteristics of a cell or organism, which characteristics are the manifestation of gene expression.

Plant Height: Plant height is taken from the top of soil to the top node of the plant and is measured in inches.

Rapid-cycling: Completion of a complete life cycle in a short time span. For instance, flowering approximately 18-21 days after planting and seed maturation after pollination occurring around an additional 3-4 weeks. Providing a total generation time (seed to seed) of approximately 7-8 weeks.

Regeneration: The development of a plant from tissue culture.

Self-compatible: The ability of a plant to self-pollinate.

Self-pollination: The transfer of pollen from the anther to the stigma of the same plant.

Single Locus Converted (Conversion) Plant: A plant, often developed through the backcrossing technique, having essentially all of the desired morphological and physiological characteristics of given variety, expect that at one locus it contains the genetic material (e.g., an allele) from a different variety. Genetic transformation may also be used to develop single locus converted plants.

Tissue culture: A composition comprising isolated cells of the same or a different type or a collection of such cells organized into parts of a plant.

VI. DEPOSIT INFORMATION

A deposit of *Brassica rapa* line B3 disclosed herein above and referenced in the claims, has been made with the American Type Culture Collection (ATCC), 10801 University Blvd., Manassas, Va. 20110-2209. The date of the deposit was Mar. 6, 2009 and the accession number for the deposited seeds of *Brassica rapa* line B3 is ATCC Accession No. PTA-9873. All restrictions upon the deposit have been removed and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Development of Self-Compatible, Rapid-Cycling Brassica rapa Plants Lacking Inbreeding Depression Rapid-cycling *Brassica rapa* plants that are self-compatible were developed through introgression of self-compatibility from a *Brassica rapa* variety into rapid-cycling *Brassica rapa* plants. Pure breeding, self-compatible lines were developed through two years of backcrossing to introgress the desired characteristics. All of the developed lines demonstrated little to no inbreeding depression and possess the same self-compatibility system introgressed from the parental *Brassica rapa* variety after 6 generations of selfing. The lines were judged to be uniform for breeding purposes. The developed lines were selected for size, healthy appearance, rapid-cycling and self-compatibility.

From the developed lines a single line designated B3 was selected for further inbreeding and development of mutant lines based on the intergenerational stability of beneficial features, such as size, healthy appearance, rapid-cycling and self-compatibility, as well as other morphological and developmental attributes. *Brassica rapa* line B3 was selfed for 11 generations, thus resulting in homozygosity at essentially all loci. *Brassica rapa* line B3 is a highly inbred, self-compatible, and self-fertile line, which is rapid-cycling, flowering (i.e., flower buds fully formed and open) at about 21 days after planting. B3 pollination was typically conducted during the 4$^{th}$ week and seeds mature approximately 3-4 weeks thereafter, yielding a total seed-to-seed generation time of approximately 8 weeks. The fact that the line persists and perpetuates these characteristics after 11 generations of inbreeding demonstrates that the B3 line does not display inbreeding depression.

Example 2

Creation and Use of Mutant Lines

The development of new self-compatible mutants provides plant variants that differ in biochemical/physiological (i.e. photosynthesis, respiration, nutrition, or other enzymes) and developmental (i.e. plant hormones, branching patterns, leaf development, or flower production) processes. Such mutants provide laboratory exercises that involve the study of different plant systems, such as plant growth or photosynthesis systems using wild type *Brassica rapa* plants compared to mutant plants.

A. Chemical (EMS) Mutagenesis

Large-scale mutagenesis of the *Brassica rapa* line B3, developed as described in Example 1, was performed to create M1 generation of mutant plants. Seeds produced from the M1 generation plants were collected and grown to produce M2 progeny plants, which were screened for mutants with educationally interesting and useful phenotypes. As mutants accumulated, they were characterized into specific classes. Such characterization included backcrossing to eliminate other lesions, allelism tests among all mutants in a particular phenotypic class, and a thorough phenotypic characterization.

Chemical mutagenesis, using ethyl methane sulfonate (EMS), was employed to generate derivatives of the self-compatible and highly inbred variety of rapid-cycling *Brassica rapa*, line B3. By screening >6500 M2 seed families, in which mutant phenotypes were expected to segregate, a collection of approximately 350 putatively mutant ("putant") lines were amassed. These lines were provisionally assigned to various phenotypic classes. The classes included both pigmentation-defective and developmental mutants. The results of the mutagenesis screen are summarized below:

Pale green (pg; pgc; pgl) putants: Among pigmentation-defective putants, a large number (approximately 50 independent isolates) were placed into the pale green (pg) category. While the majority of pg lines were uniformly pale green (as compared to the B3 wild type parent), the initial phenotype of some lines suggested tissue- or organ-specific pigmentation defects, e.g., pale green cotyledons but normal leaves (pgc) and the converse (normal cotyledons but pale green leaves, pgl).

Petal color (pec) putants: A surprisingly large number (16 lines) of putants were affected in petal color. In particular, instead of the deep and vibrant yellow pigment of the wild type, petals of pec mutant flowers were ivory-colored. Most pec mutants were uniformly miscolored, but one intriguing mutant line had mostly white petals with ribbons of normally pigmented (i.e., yellow) tissue that extend outwards from the base of the petal.

Variegated (var) isolates: Two subclasses of var putants were identified: (1) those whose patterns of variegation resulted in starkly distinct sectors of normally pigmented tissues and adjacent sectors that are pale yellow or white, and (2) those in which there existed a gradient of pigmentation, most frequently in which the deep green leaf cells of wild type gradually transitions to white cells nearer the leaf margins.

hy/ein putants: Comprising another surprisingly large class of putants, 15 lines were identified in which segregant seedlings displayed markedly extended hypocotyls shortly after germination (the hy phenotype). To varying extents, putants in this class developed such that stem segments between successive leaf nodes are similarly elongated as compared to wild type (elongated internodes, ein). Complementation tests among 9 ein mutants and including a previously described *Brassica rapa* ein mutant (Devlin et al., 1997 *Plant Mol. Biol.* 34:537-547) indicate that all mutants tested affect the phytochrome B (PhyB) locus, whose gene product has been shown to play a key role in regulation of photomorphogenic response pathways. Sequence analysis was performed for a subset of ein mutants, selected on the basis of phenotypic severity. Assuming that the published phyB mutant constitutes a null allele (Devlin et al. report that it contains an approximately 500 bp deletion of undefined sequence immediately upstream of the translation start site), the preliminary results have identified a correlation between the nature of EMS-induced mutations and phenotypic severity. That is, the most severe ein mutant has been shown to carry a G to A transition that creates a stop codon midway through the second exon of PhyB, whereas a less severely affected ein mutant has been shown to harbor a missense (Thr to Ile) mutation within the first exon.

Apetala (ap) putants: Two isolates were identified in which flowers failed to form petals (ap phenotype).

Abnormal leaf (ale): Leaves of ale mutant plants were tightly curled, often to the extent that leaf tissues formed a coherent mass that is club-like in appearance. In addition, the stems of ale mutants typically sported ectopic fringes of leaf-like tissue. Interestingly, those phenotypes seemed to be specific to the vegetative growth phase, since inflorescence organs and tissues were essentially normal and mutant plants were fully fertile. The B3 ale mutant was outcrossed to the mapping line to generate a segregating F2 population, and the nascent collection of SSR markers was used to map the mutant locus among the 10 chromosomes of Brassica rapa. The ale mutant phenotype was robust and readily distinguishable from the wild type. Furthermore, the phenotype was dosage-dependent, such that the homozygote was more severely affected than the heterozygote. The ale mutant thus epitomized the behavior of a dominant allele.

Miscellaneous class: Numerically, this catch-all class of putants was the largest that resulted from the mutagenesis screens, consisting of isolates whose phenotypes were subtle but potentially interesting. Descriptive names were assigned as follows: twisted cotyledons, spiral stem, white stem, dwarf gigantica, leaf factory, abnormal leaf club pod, etc.

The above mutagenesis screen was followed by characterization, clean-up, and evaluation of the putant lines isolated. It is understood that many candidate lines resulting from a genetic screen may not, upon subsequent analysis, prove to be useful or interesting. M2 segregants suitable for use in a classroom teaching environment, for instance with phenotypes readily identifiable by young students (i.e. 4th grade), were transplanted and self-pollinated. In addition, most lines were backcrossed to the wild type B3 parental line to initiate genetic characterization and cleanup.

As part of the further characterization of putant lines obtained, experiments were performed to determine if the initial M2 phenotypes were heritable. For instance, seeds derived from self-pollination of M2 segregants were planted alongside wild type B3. The resulting plants were compared and the mutant phenotype, if evident, was evaluated with respect to its potential utility. For instance, to determine if the phenotype was robust, readily identified, uniformly evident, segregating, or poorly penetrant and what effects there were on plant vigor and fecundity.

Additionally, experiments were conducted to determine the dominance relationship between the mutant allele and the wild type by backcrossing the F2 progeny (M2 segregants×B3), which were then grown and inspected for indications of dominance, semi-dominance and segregation. Furthermore, the patterns of inheritance (simple Mendelian or otherwise) were determined. In particular, the F1 plants of backcrosses were selfed to generate an F2 population that was scored to infer the nature of the mutant alleles. Thus, an F2 that produced ¼ mutant segregants indicated that the mutant allele represented a simple recessive character; an F2 that yielded ¾ mutant segregants reflected the activity of a dominant allele. Aberrant (i.e., apparently non-Mendelian) segregation ratios among F2 progeny may have been indicative of multigenic traits or those that were transmitted uniparentally.

Experiments to determine to what extent is the mutant phenotype conditioned by the presence of unrelated mutations induced by EMS were also carried out. For instance, F2 (formally, bc1F2) mutant segregants were used to generate a 2nd backcross generation (bc2F1) that was selfed and whose progeny segregants (bc2F2) were grown adjacent to M3, bc1F2, and B3 plants.

Additional experiments were also carried out to determine the allelic relationships among mutant lines with similar phenotypes. In particular, M3 mutants that recapitulated M2 phenotypes were intercrossed to initiate complementation tests. The F1 plants were grown and inspected to infer allelism (i.e., all F1 plants phenotypically mutant) or independent loci (i.e., all F1 phenotypically wild type). F1 plants were self-pollinated and the resulting F2 plants were scored to confirm conclusions drawn from the F1. If the loci were allelic, all F2 were expected to likewise be mutant; if independent, a 9:7 wild type: mutant ratio was expected; if independent mutant loci had additive effects a 9:6:1 ratio was expected, wherein 1/16 of segregants displayed a phenotype that was more severe than either of the presumptive F2 single homozygotes.

Through these experiments the collection of approximately 350 putant lines was pared down to a set of approximately 50 confirmed mutant lines that were judge as potentially useful. The majority of lines that were discarded along the way simply failed to recapitulate the phenotype observed in the M2. As noted above, that is a typical result of any genetic screen. Other lines were abandoned because the phenotypes were subtle and hard to distinguish from wild type, or the plants were so feeble that teachers would not likely be willing or able to coddle the plants to reproductive maturity. Some mutants were dropped because, upon backcrossing, the mutant phenotypes that appeared to be robust in the M3 were attenuated to the point of uselessness in the bc1F2 generation.

Among the remaining lines, the pg, pec, and ein mutant classes comprise the largest classes. The results from the above experiments suggest that there are many discrete loci that, when mutant, yield those common phenotypes.

Complementation tests among all pg and pec lines will be performed. Based on the early results of complementation tests among ein mutants that indicated allelism of all mutants, it was expected that saturation with regard to mutant recovery may have been reached. However, only a small minority of pg and pec mutant lines (3/17 and 2/18, respectively, among those in which the M3 recapitulated the M2 phenotypes) were shown to be allelic. Assuming that robust pg and pec phenotypes are maintained through the course of backcrossing, these mutants will be used to populate the Brassica rapa genetic map with visible markers useful for developing principles of linkage. At a minimum, the pg and pec mutant collections will serve to illustrate the notion that there are often multiple biochemical steps in a genetic pathway that leads to a trait. Alternatively, there may be other instances in which pathways operating in parallel are required for the proper elaboration of phenotype.

All mutant lines will proceed through three generations of backcrosses and analysis, pairwise complementation tests will be completed, and evaluation the remaining lines for use in particular lesson modules will be performed. Additionally, certain double mutant combinations for use in classrooms have been constructed. For instance, an ale/pg double mutant line was developed and field tests will be performed.

B. Introgression of Previously Characterized Brassica rapa Dwarf Mutant Alleles

Dwarf (dwf) mutants provide a great tool to teach biochemical genetics. Many dwf mutants are deficient in the biosynthesis or sensing of the plant hormone gibberellin. Gibberellin is a steroid-like hormone with several specific steps in its pathway of synthesis, and thus there are several targets that, when mutated, produce the dwf phenotype. Complementation testing among these mutants illustrates the concept of a biochemical pathway.

To further illustrate biochemical genetics, dwf mutant plants can be treated with gibberellin to distinguish mutants defective in biosynthesis (restored to a normal phenotype) from those defective in signal transduction (no response to treatment). Furthermore, treatment of a collection of mutants that have lesions at various stages of the biosynthetic pathway with gibberellin precursors will reveal that fewer mutants will be restored as one treats with precursors earlier in the pathway, illustrating the order in which the enzymes act in the pathway.

Mutants in which the gibberellin signal transduction pathway is constitutively activated (even in the absence of gibberellin) may also be created. These mutants will grow very tall. This will provide an opportunity to develop exercises to illustrate epistasis, as such signal transduction mutations are typically epistatic to the dwf mutations.

The EMS mutagenesis, described above, provided a collection of mutants useful for teaching genetic concepts. However, certain mutant classes were notably not recovered in the above screens. In particular, no confirmed dwf mutant lines were identified despite the fact that (a) many candidate lines identified among M2 families were assessed for such a phenotype; and (b) several dwf mutants of *Brassica rapa* have been described in the scientific literature and were expected to be recovered (Zanewich et al., 1991, *J. Plant Growth and Regulation* 10:121-127; Muangprom et al., 2006, *Molecular Breeding* 17:101-110, and references therein).

Two explanations might account for the lack of isolated dwf mutants via EMS mutagenesis. First, growth and development of M2 families is "noisy," particularly because the level of EMS used to treat B3 seeds (0.5-0.7%) is the maximum level able to be used and yet maintain fertility among M1 plants. Progeny seeds borne by those plants consequently suffer from a relatively difficult gestation and the effects can often be seen among M2 plants; that "noise" may also account for a significant number of false-positives among the initial collection of putants.

Second, one known dwf mutant, rosette (ros), owes its diminutive and distinctive mutant phenotype to an inability to synthesize the plant hormone gibberellic acid (GA). A secondary consequence of GA deficiency in ros mutants is a prolonged period of seed dormancy in homozygotes. Thus, ros mutant alleles may, in fact, have been present within the M2 families, but if the seeds bearing ros mutant segregants did not germinate or did so only much later than phenotypically wild type siblings, they would likely have been missed.

Nonetheless, there is considerable merit in adding dwf mutant alleles to the collection mutants and thus introgression from existing dwf mutant stocks was performed. dwf1 and dwf2 are GA-insensitive mutants, while ros is GA-responsive, and all three mutant alleles are available in the Wisconsin Fast Plant variety of *Brassica rapa*. These lines were crossed to the *Brassica rapa* line B3 and will be backcrossed repeatedly in order to minimize the extent of unrelated genetic variation contributed by the Wisconsin Fast Plant parents.

C. Exploiting Morphological Diversity Among Cultivated *Brassica Ram as a Source of Genetic Variation*

*Brassica rapa* is a species whose subfamilies exhibit a remarkably broad range of morphological diversity. Included among the "veggie" rapas are turnips, various mustards, and salad greens such as Chinese cabbage and bok choi. *Brassica rapa* also includes several agronomically important oil seed crops such as canola and Yellow Sarson. Exploratory experiments were initiated in order to investigate the potential of crosses to yield interesting allelic variants. In particular, *Brassica rapa* line B3 was crossed to representatives of the nine recognized *rapa* subspecies. The F1 of such crosses were grown and inspected for evidence of dominant traits that may be of interest, and F2 populations will be examined to identify well-behaved and distinctive Mendelian traits.

This approach has led to the successful introgression of a recessive allele from Yellow Sarson (*Brassica rapa* subspecies *trilocularis*) that results in yellow seed coats when homozygous. Breeding was advanced to the second backcross generation (following an initial B3×Sarson cross) and the behavior of the "mutant" allele was examined in a genetic background in which approximately 87.5% of the genome was derived from the B3 lineage.

The trait is transmitted as a simple recessive allele as are most of the existing EMS-generated alleles, but the yellow seed coat phenotype presents interesting twists that will be particularly useful in classrooms for several reasons.

First, seed coat color is a largely maternally-specified trait (with a small component that is not maternal as discussed below) independent of the genotype of the enclosed embryo. Thus, it is intuitive, but wrong, to assume that plants grown from yellow seeds will breed true and necessarily produce yellow seeds. That misguided intuition is quite compelling, and dispelling it requires the student or breeder to think hard about the underlying genetics and the relationship of genotype and phenotype.

Second, it was shown that the seed coat color trait in the mutant is evocative of the xenia effect, in which, generally speaking, the genes of the male parent in a cross exert a direct effect on the development of fruit or seeds. Xenia is a well-known but poorly understood phenomenon in plant breeding circles. The preliminary results offer some hope that the xenia effect observed may be instructive in the classroom.

Thus, a known yellow-seeded mother plant (genotype bb) was crossed using pollen from a heterozygous F1 derived from a cross of B3×Yellow Sarson. As predicted, approximately 50% of the resulting seeds demonstrated coats that were darker brown than the pure yellow seed coats of siblings.

This simple cross will be a useful way to quickly get across to students the notion that alternative alleles segregate during meiosis. Crosses to set the introgression will continue and the potential of this exercise will be evaluated when the allele is more thoroughly integrated in a B3 genetic background.

D. Additional Mutants

Numerous additional classes of mutants can be produced by the above methods. For instance, albinos provide a simple example of a deleterious recessive mutation that prevents survival to maturity. When used in classroom exercises, students can quickly see a 3:1 segregation pattern. They can save seed from the non-albino plants and find that ⅔ of them produce offspring that segregate albinos but from the other ⅓ the albino trait is never seen again. Use of an albino mutant provides students the opportunity to genotype the parents based upon their progeny, requiring them to work back from observation to a model. Embryo lethal mutants provide another model of this. Because the albino or embryo lethal mutant phenotype is identifiable very early in development, they also provide rapid feedback where time and/or space might be limiting.

Example 3

Development of Robust Molecular (PCR-Based) Assays for Mapping Genetic Traits in *Brassica rapa* and Development of Tools for Teaching Molecular Genetics The plants of the invention may also be used to develop tools for learning molecular genetics. From plant breeding to tracking and cloning loci involved in human disease, gene mapping using DNA sequence polymorphisms is a key component of modern molecular genetics. Experiments were performed intended to identify and assemble a collection of PCR-based assays that will enable students to conduct genetic mapping experiments in *Brassica rapa*. The goal was to identify oligonucleotide primer pairs that reliably detect simple sequence repeat (SSR) polymorphisms between *Brassica rapa* line B3 and an alternative *Brassica rapa* variety. While there are several high-density maps published in the scientific literature (1-2 cM resolution; approximately 1200 cM total genetic map distance), none have included the present *Brassica rapa* derivative. Furthermore, whereas labs may have attempted to alter PCR profiles to suit the conditions necessary for a given primer pair, or the relative luxury of polyacrylamide gels or even capillary electrophoresis to detect reaction products of F2 segregants, the intended PCR-based assays should use a uniform and straightforward thermocycling profile and standard agarose gel electrophoresis and reliably and unambiguously distinguish among homozygous and heterozygous genotypes in F2 individuals produced through crosses.

R500/Yellow Sarson was selected for outcrossing and mapping purposes based on a preliminary survey of several *Brassica rapa* alternatives, in which the R500 line consistently yielded a greater incidence of detectable polymorphic alleles. A molecular genetic map of the present *Brassica rapa* line B3 has been developed and additional molecular resources have been developed, including approximately 20 primer pairs that reproducibly yield clearly polymorphic reaction products. Further molecular resources will be developed, including a molecular map of approximately 20 cM resolution. If evenly distributed among the ten chromosomes of *Brassica rapa*, that density would be sufficient to localize any mutant locus selected for analysis.

Figure 2:
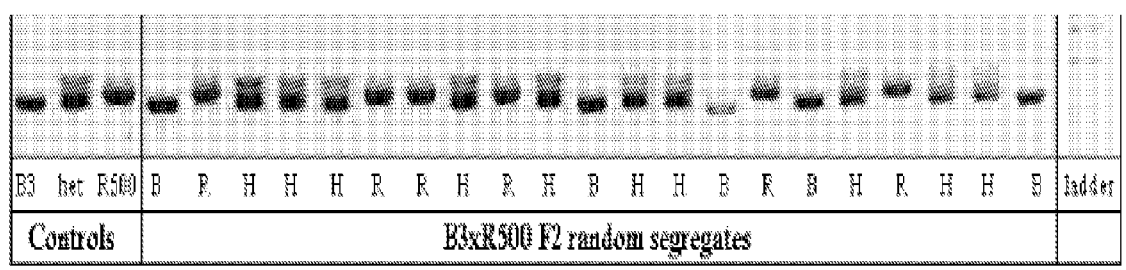
FIG. 2: Analysis of genotypes among F2 segregants derived from an initial B3×R500 cross.

A further task will be to verify linkage relationships among polymorphic molecular markers. The published scientific literature regarding SSR loci in *Brassica rapa* is at times in conflict, such that polymorphic loci have in some cases been assigned to different *Brassica rapa* chromosomes by different research groups using the same primer sequences. Given that uncertainty, it is essential to determine the linkage relationships and map positions of all markers that will be offered for use in classrooms. In order to do this, analysis of genotypes among F2 segregants derived from an initial B3×R500 cross was performed (FIG. 2).

To additionally enable the development of tools in this area, mutants of the B3 line can be crossed to a polymorphic line and the mutant locus can be mapped in the resulting F2 population. The resolution of the mapping is a function of the number of polymorphic markers available. Because certain varieties of *Brassica rapa* are used as crops there are labs worldwide developing markers for breeding programs (e.g., the Multinational *Brassica* Genome Project) and there should be a sufficient number of markers that will be polymorphic in order to develop meaningful mapping exercises.

Genes that have been mutated in specific *Brassica rapa* mutants will be identified and novel markers close to these genes will be developed to create exercises that illustrate the type of fine mapping that leads to gene discovery. Advances in *Arabidopsis* research provide a resource for gene discovery in *Brassica rapa*. As expected for plants that diverged less than 20 million years ago, there is a high level of nucleotide sequence conservation (about 85%) in coding regions and extensive synteny (average 2.1 Mbp) between *Arabidopsis* and *Brassica rapa*. Many of the mutant phenotypes will match those of well-characterized *Arabidopsis* mutants and thus multiple candidate genes will be available to evaluate. A large number of end-sequenced *Brassica rapa* BACs are being aligned with the *Arabidopsis* genome (www.brassica-rapa.org). It will therefore be possible to obtain BACs that are likely to contain the candidate genes and use these to clone the candidates as well as to provide surrounding regions of DNA to use for marker development. The exercises developed will illustrate the principles upon which human genomics projects, such as the HapMap Project, are based.

Example 4

Comparison of Rapid-Cycling and Self-Compatible *Brassica rapa* Plants with Current Rapid-Cycling, Self-Incompatible Classroom Model Plants Several features of the *Brassica rapa* B3 lineage are distinct from the currently available rapid-cycling, classroom model plants, such as Wisconsin Fast Plants, and contribute to the line's utility as a model organism for research in genetics. For instance, *Brassica rapa* line B3 lacks the genetic self-incompatibility system in Wisconsin Fast Plants. The consequent capacity for self-fertilization in line B3 greatly simplifies genetic manipulations. Additionally, through the course of the breeding program described in Example 1, *Brassica rapa* line B3 has been extensively inbred. There is therefore essentially no residual heterozygosity in the genome of line B3. Furthermore, *Brassica rapa* line B3 populations are relatively more uniform in appearance and phenotypic variation than the current rapid-cycling classroom model plants due to the increased homozygosity and thus induced mutations are readily apparent.

The genetic self-incompatibility seen in other rapid-cycling classroom models, such as Wisconsin Fast Plants, renders them a poor model system for genetics exercises as might be conducted in educational settings, and effectively precludes the use of chemical mutagenesis approaches to generation of interesting mutant derivatives. However, the absence of genetic self-incompatibility and history of extensive inbreeding of *Brassica rapa* line B3 overcome the limitations of other classroom model plants for education in genetics. Line B3 is self-compatible and self-fertile, thus facilitating straightforward generation, propagation, and analysis of mutant alleles. The utility of self-compatibility is particularly evident given the successful implementation of chemical mutagenesis to isolate allelic variants, as described in Example 2. Following exposure to the mutagen EMS, GC-AT transition mutations are essentially propagated in the heterozygous conditions. Self-pollination of plants grown from mutagenized seeds results in homozygosis at affected loci. Mutant phenotypes potentially useful for classroom exercises can thus be identified as segregants in the next generation. As described in Example 2, over 6,500 seed families produced by self-pollination of mutagenized plants and have identified over 350 lines in which heritable mutant alleles have readily apparent effects on plant phenotype. The necessity for mass-sib mating in self-incompatible classroom models, such as Wisconsin Fast Plants precludes such a straightforward means to achieve homozygosity. Finally, given the genetic uniformity of *Brassica rapa* line B3 after 11 generations of selfing, as described in Example 1, theeffects on growth and development of single-locus allelic variants can be determined without the complications imposed by a variable genetic background.

To exemplify the differences between the self-compatible *Brassica rapa* plants of the current invention and the self-incompatible *Brassica rapa* plants, the ability of each plant to produce flowers and seeds under certain pollination conditions were determined. For these experiments, seeds of *Brassica rapa* Wisconsin Fast Plants and line B3 were planted in standard 11"×22" flats fitted with 48-cell plastic inserts. Wisconsin Fast Plant seeds were purchased from Carolina Biological Supply and B3 seeds were produced as described in Example 1 and correspond to the 11$^{th}$ generation obtained by self-pollination. Three separate flats (each containing up to 24 Wisconsin Fast Plants and 24 B3 plants) comprised discrete treatment groups that differ with respect to means of pollination. In one case (mass-sib mating), bee sticks were used to intercross among flowers of all plants in each subpopulation. The resulting seed set was used to define 100% fecundity of the self-incompatible Wisconsin Fast Plant variety. In a second case, flowers on plants of each subpopulation were self-pollinated. By comparison to the respective average seed yield (per pollinated flower) obtained by mass-sib mating, the results indicated the extent to which genetic self-incompatibility prevents self-pollination of Wisconsin Fast Plant flowers and, likewise, indicates the absence of genetic self-incompatibility in B3. It should be noted that apparent self-fertility of Wisconsin Fast Plants in cases where flowers set seed, may have been due to pollination of relatively immature flowers, whose self-incompatibility mechanisms had not yet been fully expressed. In addition, given the close proximity of sibling plants, the possibility of unintended cross-pollination cannot be excluded. Finally, a third treatment group was comprised of plants that were unmanipulated throughout the plant life cycle. The average seed set in this treatment group indicated the propensity for spontaneous self-fertility.

In the first two treatment groups, two rounds of pollinations were conducted, first when approximately 3-5 flowers (on average) were open on most plants of a subpopulation, and a second round approximately two days thereafter, to yield approximately 10 pollinated flowers/plants. Further flower formation was prevented in those treatment groups by excision of the inflorescence meristem following the second round of pollinations. For the unmanipulated subpopulations (whole meristems had not been manually terminated), average seed set was determined by inspection of the first 10 flowers formed by each plant (fewer flowers were observed in some cases where the apical meristem had spontaneously halted flower formation). Results of the comparison are shown in Table 1.

TABLE 1

Comparison of self-fertility and fecundity of *Brassica rapa* varieties B3 and Wisconsin Fast Plants (WFP)

Average seeds/flower (+/−st. dev.) in treatment group$^a$

| | Mass-Sib Mating$^b$ | | | Assisted Self-Pollination$^c$ | | | Spontaneous Self-Pollination$^d$ | | |
|---|---|---|---|---|---|---|---|---|---|
| | # Plants | # Flowers | Avg. # Seeds/Flower | # Plants | # Flowers | Avg. # Seeds/Flower | # Plants | # Flowers | Avg. # Seeds/Flower |
| B3 | 9 | 69 | 10.7 +/− 4.5 | 15 | 110 | 8.1 +/− 4.8 | 16 | 111 | 4.0 +/− 4.8 |
| WFP | 16 | 108 | 18.0 +/− 5.9 | 20 | 183 | 0.5 +/− 1.7 | 23 | 203 | 0.2 +/− 0.9 |

WFP = Wisconsin Fast Plants $^a$Average number of seeds observed among the first 10 flowers of each plant (<10 if apical meristem terminated prior to producing 10 flowers).

$^b$Flowers of all plants in B3 or WFP subpopulations intercrossed by using bee sticks.

$^c$Individual flowers of plants in B3 or WFP subpopulations pollinated using forceps to extract anthers.

$^d$Plants in each subpopulation were wholly unmanipulated throughout the plant life cycle.

What is claimed is:

1. A *Brassica rapa* plant that is self-compatible, rapid-cycling and lacks inbreeding depression relative to Wisconsin Fast Plants, wherein the *Brassica rapa* plant comprises the self-compatibility trait found in line B3, wherein a sample of seed of said line B3 has been deposited under ATCC Accession No. PTA-9873.

2. The plant of claim 1, wherein the plant is a plant of line B3 or a progeny thereof; wherein a sample of seed of said line B3 has been deposited under ATCC Accession No. PTA-9873.

3. The plant of claim 1, wherein the plant is inbred.

4. A plant part of the plant of claim 1.

5. The plant part of claim 4, wherein said part is selected from the group consisting of a protoplast, ovule, cell, pollen grain, embryo, cotyledon, hypocotyl, meristem, root, pistil, anther, flower, stem, pod or petiole.

6. A tissue culture of regenerable cells of a plant of claim 1.

7. The tissue culture according to claim 6, comprising cells or protoplasts from a plant part selected from the group consisting of embryos, meristems, cotyledons, pollen, leaves, anthers, roots, root tips, shoots, pistil, flower, seed and stem.

8. A method of propagating the plant of claim 1, comprising crossing the plant with itself or a second plant.

9. A method of vegetatively propagating a plant of claim 1 comprising:

(a) collecting tissue capable of being propagated from a plant of claim 1;

(b) cultivating said tissue to obtain proliferated shoots; and (c) rooting said proliferated shoots to obtain rooted plantlets.

10. The method of claim 9, further comprising growing plants from said rooted plantlets.

11. A method of producing a mutant allele comprising
(a) obtaining a plant of claim 1 or tissue thereof;
(b) subjecting said plant or tissue thereof to mutagenesis; and
(c) recovering a plant comprising a mutant allele.

12. The method of claim 11, wherein mutagenesis comprises use of a mutagen selected from the group consisting of gamma irradiation and chemical mutagenesis.

13. A plant produced by the method of claim 11, wherein said plant comprises said mutant allele and is self-compatible, rapid-cycling and lacks inbreeding depression relative to Wisconsin Fast Plants, wherein said *Brassica rapa* plant comprises the self-compatibility trait found in line B3, wherein a sample of seed of said line B3 has been deposited under ATCC Accession No. PTA-9873.

14. A method of producing a self-compatible, rapid-cycling, *Brassica rapa* plant lacking inbreeding depression comprising:
(a) crossing the plant of claim 1 with a second plant to produce progeny plants; and
(b) selecting at least a first progeny plant from step (a) that comprises a desired trait.

15. The method of claim 14, further comprising:
(c) backcrossing the selected first progeny plant from step (b) with the plant of claim 1; and
(d) selecting at least a first backcross progeny plant from step (c) that comprises the desired trait.

16. The method of claim 14, wherein the desired trait is selected from the group consisting of a pigmentation-defective mutant trait and developmental mutant trait.

17. The method of claim 14, wherein the desired trait is selected from the group consisting of embryo lethal, albino, leaf shape, leaf number, leaf color, variegated leaf, flower shape, flower number, flower color, seed color, seed shape, tissue- or organ-specific pigmentation, a photosynthesis trait, internode shape, hypocotyl shape, cotyledon shape, stem shape, pod shape, dwarf and over-sized.

18. The method of claim 14, wherein the desired trait is due to a mutation in a gene encoding a protein involved in a biochemical or developmental pathway.

19. A plant produced by the method of claim 14, wherein said plant comprises said desired trait and is self-compatible, rapid-cycling and lacks inbreeding depression relative to Wisconsin Fast Plants, wherein said *Brassica rapa* plant comprises the self-compatibility trait found in line B3, wherein a sample of seed of said line B3 has been deposited under ATCC Accession No. PTA-9873.

20. An educational kit comprising the plant of claim 1 or a seed that produces said plant.

21. A *Brassica rapa* plant of line B3, further comprising a single locus conversion, wherein the plant otherwise comprises essentially all of the physiological and morphological characteristics of *Brassica rapa* line B3, and wherein a sample of seed *Brassica rapa* line B3 has been deposited under ATCC Accession No. PTA-9873.

22. A plant produced by the method of claim 8, wherein said plant is self-compatible, rapid-cycling and lacks inbreeding depression relative to Wisconsin Fast Plants, wherein said *Brassica rapa* plant comprises the self-compatibility trait found in line B3, wherein a sample of seed of said line B3 has been deposited under ATCC Accession No. PTA-9873.

* * * * *